(12) United States Patent
Frikart et al.

(10) Patent No.: US 8,758,240 B2
(45) Date of Patent: Jun. 24, 2014

(54) SYSTEM WITH A PORTABLE PATIENT DEVICE AND EXTERNAL OPERATING PART

(75) Inventors: Marcel Frikart, Bern (CH); Markus Jungen, Bolligen (CH); Matthias Ehrsam, Bolligen (CH); Kurt Friedli, Lyssach (CH)

(73) Assignee: Roche Diagnostics International AG, Rotkreuz (CH)

( * ) Notice: Subject to any disclaimer, the term of this patent is extended or adjusted under 35 U.S.C. 154(b) by 507 days.

(21) Appl. No.: 11/608,936

(22) Filed: Dec. 11, 2006

(65) Prior Publication Data

US 2007/0142767 A1 Jun. 21, 2007

(30) Foreign Application Priority Data

Dec. 12, 2005 (EP) .................................... 05027063

(51) Int. Cl.
 *A61B 5/00* (2006.01)
 *G06F 19/00* (2011.01)
(52) U.S. Cl.
 CPC ................................ *G06F 19/3406* (2013.01)
 USPC ............................. 600/301; 600/300; 604/65
(58) Field of Classification Search
 USPC ................. 600/300–301; 128/903–905, 920; 705/2–4; 340/573.1; 607/62; 604/65–67
 See application file for complete search history.

(56) References Cited

U.S. PATENT DOCUMENTS

| | | | |
|---|---|---|---|
| 6,579,231 B1 * | 6/2003 | Phipps .......................... | 600/300 |
| 6,599,241 B1 * | 7/2003 | Murphy ........................ | 600/300 |
| 6,699,187 B2 * | 3/2004 | Webb et al. .................... | 600/300 |
| 6,803,928 B2 * | 10/2004 | Bimber et al. ................. | 715/757 |
| 7,713,240 B2 * | 5/2010 | Istoc et al. ..................... | 604/131 |
| 2001/0025189 A1 | 9/2001 | Haueter et al. | |
| 2002/0019584 A1 * | 2/2002 | Schulze et al. ................ | 600/300 |
| 2003/0109286 A1 | 6/2003 | Hack et al. | |
| 2003/0144034 A1 * | 7/2003 | Hack et al. ..................... | 455/566 |
| 2003/0144581 A1 | 7/2003 | Conn et al. | |
| 2004/0039255 A1 * | 2/2004 | Simonsen et al. ............. | 600/300 |
| 2004/0122353 A1 * | 6/2004 | Shahmirian et al. ............ | 604/65 |
| 2004/0147818 A1 * | 7/2004 | Levy et al. ..................... | 600/300 |
| 2004/0260233 A1 | 12/2004 | Garibotto et al. | |
| 2005/0062760 A1 * | 3/2005 | Twede .......................... | 345/619 |
| 2005/0113648 A1 * | 5/2005 | Yang et al. .................... | 600/300 |
| 2005/0119604 A1 * | 6/2005 | Bonney et al. ................. | 604/19 |
| 2005/0193396 A1 * | 9/2005 | Stafford-Fraser et al. .... | 719/328 |
| 2005/0277872 A1 * | 12/2005 | Colby et al. ................... | 604/67 |
| 2006/0013462 A1 * | 1/2006 | Sadikali ........................ | 382/132 |
| 2006/0047192 A1 * | 3/2006 | Hellwig et al. ............... | 600/365 |
| 2006/0094936 A1 * | 5/2006 | Russ .............................. | 600/300 |
| 2006/0253300 A1 * | 11/2006 | Somberg et al. .................. | 705/2 |
| 2006/0253301 A1 * | 11/2006 | Simms et al. ...................... | 705/2 |
| 2006/0293571 A1 * | 12/2006 | Bao et al. ...................... | 600/300 |
| 2007/0060869 A1 * | 3/2007 | Tolle et al. ..................... | 604/65 |
| 2007/0060871 A1 * | 3/2007 | Istoc et al. ..................... | 604/65 |
| 2007/0098565 A1 * | 5/2007 | Parsee et al. ................. | 417/44.1 |
| 2007/0179434 A1 * | 8/2007 | Weinert et al. ................. | 604/66 |
| 2009/0247931 A1 * | 10/2009 | Damgaard-Sorensen ...... | 604/19 |

FOREIGN PATENT DOCUMENTS

| | | |
|---|---|---|
| CN | 1639992 A1 | 7/2005 |
| WO | 01/28416 A | 4/2001 |

* cited by examiner

*Primary Examiner* — Bill Thomson
*Assistant Examiner* — Bobby Soriano
(74) *Attorney, Agent, or Firm* — Dinsmore & Shohl LLP

(57) ABSTRACT

A patient system including a first patient device for being carried by a patient and a second patient device arranged remotely from the first patient device, wherein a user interface of the first patient device is provided separately from the first patient device on the second patient device.

21 Claims, 2 Drawing Sheets

SYSTEM WITH A PORTABLE PATIENT DEVICE AND EXTERNAL OPERATING PART

CROSS-REFERENCE TO RELATED APPLICATION

This application claims the benefit of European Patent Application No. 05027063.6, filed on Dec. 12, 2005, the content of which is incorporated in its entirety by reference herein.

BACKGROUND

The present invention relates to medical devices, and to methods of making and using such devices. More particularly, it relates to medical devices and systems comprising portable components or features for treating patients, wherein a patient can carry on as completely as possible with normal day-to-day activities. More particularly, the present invention relates to devices for administering, delivering, infusing, injecting or dispensing substances, and to methods of making, using and operating such devices.

Portable patient devices are known for a multiplicity of applications, for example for blood pressure measurement, pulse measurement, ECG recording and medication supply. These patient devices are now an important aid in diagnosis and therapy, allowing a patient to go about everyday life without great restrictions, while offering doctors informative measurements under everyday conditions.

An example of a patient device for supplying medication is an insulin pump, for example the Accu-Chek® insulin pump from Roche Diagnostics GmbH, Germany. A patient carries the insulin pump, generally on or near their body. Via a thin tube and a cannula is placed under the skin, the insulin pump delivers insulin continuously to the body. Microprocessors control a motor which moves a plunger in an insulin vial via a threaded rod, for example every three minutes or on demand. This movement, which corresponds to a respectively programmed basal rate, i.e. the patient's basic insulin demand, supplies the body with the required amount of insulin. The patient can adjust and operate the insulin pump via a user interface, including a display unit (display) and buttons.

These patient devices can be worn or carried relatively inconspicuously and discreetly by the patients. In the course of a day, the patients occasionally need to adjust the devices or check the settings, which under certain circumstances is not possible to do discreetly.

SUMMARY

An object of the present invention to allow patients to be able to adjust and check patient devices (e.g., therapeutic and diagnostic devices) more discreetly. To permit this in the exemplary embodiments of a patient system as described herein, the user interface of the patient device can be represented or presented separately from the patient device, for example on a separate device arranged or carried remotely from the patient device. The patient can operate the separate device, which may be thought of as a secondary or peripheral device, e.g. a component of a mobile telephone, conveniently and discreetly.

One aspect of the present invention relates to a patient system which has a first patient device portable or carried on or in the body of a patient and a second patient device, which also may be referred to herein as the operating device, arranged remotely from the first patient device. Each patient device comprises a communication module for data transmission via a transmission link. The first patient device comprises a data-processing module for communication with a user interface for the first patient device. The second patient device is configured such that it represents the user interface for the portable first patient device.

A further aspect of the present invention relates to a method for operating a patient system in which a first patient device portable on the body of a patient and a second patient device arranged remotely from the first patient device can communicate with one another via a transmission link. A data-processing module for communication with a user interface for the first patient device is operated in the first patient device. Data relating to the user interface and the devices are communicated between the first and second patient devices, and the user interface for the first patient device is represented on the second patient device.

In some embodiments, the remotely arranged device may be a device provided specially for this patient system, which is used only for representing the user interface. This function of the device may nevertheless also be integrated in a device which is known per se, e.g., a mobile telephone (smart phone), computer, e.g., desktop computer, pocket PC, notebook, PDA, or blood sugar meter, and/or appropriate software and a software processing or using devices. Such a modified device accordingly has its own function, for example that of a mobile telephone, and additionally the function of an operating device for the patient device.

Depending on the embodiment of the present invention, the user interface may be fully or partially integrated in the patient device. Sometimes undesired intervention directly on the patient device is therefore unnecessary. The patient device can therefore also be smaller since only a minimal user interface, for example a smaller display, is necessary in the patient device. A display function or feature may be entirely omitted in some exemplary embodiments. Such a patient device can therefore be carried even more discreetly by the patient.

Since the user interface is represented externally, the size of the representation of the user interface is no longer subject to the size restrictions of the patient device. The user interface may thus be represented, for example, on a larger display (for example on a mobile telephone (smart phone) or a computer (e.g., desktop computer, pocket PC, notebook, PDA)). This may be especially valuable for diabetic patients, who often also have restricted eyesight, since they can see the larger representation better.

In one embodiment, the operating device described herein has at least the same functionality as the user interface of the patient device. Depending on the exemplary embodiment and application, the operating device may serve as a remote control, and/or monitor and status display for the patient device. In some embodiments, it may therefore also be used to modify parameters and settings of the patient device.

DETAILED DESCRIPTION

Without restricting the scope of the present invention, various ways of embodying the invention are described below with reference to an insulin pump.

An insulin pump, however, is only one example of a patient device which a patient would like to carry and operate as discreetly as possible. Pumps for other medications, glucose meters, lactate meters, blood pressure meters and ECG devices are further examples of patient devices which may be embodied in accordance with the present invention.

With regard to fastening, mounting, attaching or connecting components of the present invention, unless specifically described as otherwise, conventional fasteners such as threads, pins and the like may be used. Other suitable fastening or attachment structures and methods include friction fitting, adhesives, welding and soldering. Any of the components of the electrical system(s) of the present invention may be, or be made up from, suitable electrical components or devices unless otherwise indicated. This is intended to include electrical components and circuitry, wires, connections, sensors, communication devices, computers, microprocessors, circuit boards, displays, etc. Generally, unless specifically otherwise disclosed or taught, the materials for the various components of the present invention, for example the case(s) and operable components, may be selected from appropriate materials such as metals, metallic alloys, plastics, etc.

Figure 1:
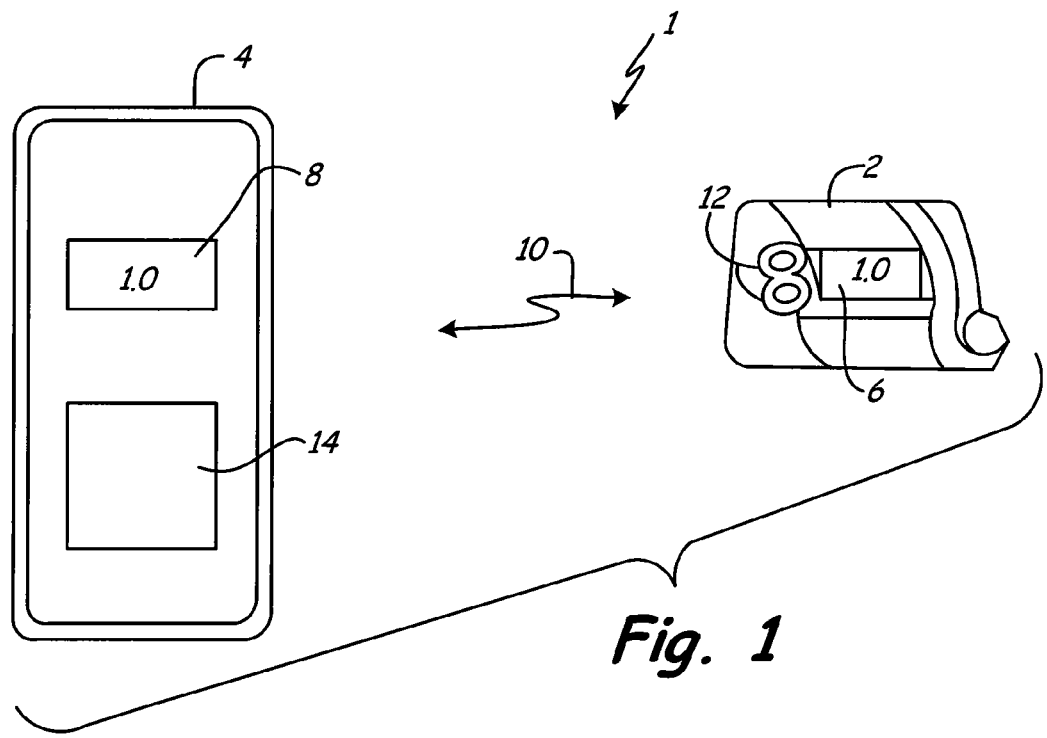
FIG. 1 is a schematic representation of an exemplary embodiment of a patient system comprising a patient device and an operating device in accordance with the present invention.

FIG. 1 is a schematic representation of an exemplary embodiment of a patient system 1 comprising a first patient device 2 and a second patient device, or operating device 4. The patient device 2 has a display unit 6, referred to below as display 6, and operating buttons 12. The operating device 4 likewise has a display unit 8, likewise referred to below as display 8, and a keypad 14.

The display 6 and the operating buttons 12 are part of the user interface of the patient device 2. The user interface is generally employed for the interaction between a patient and the patient device 2, and, inter alia, allows the patient to operate the patient device 2. The user interface represents information optically or acoustically, for example. The patient may react to the represented information depending on the status of the patient device 2, for example by pressing the operating buttons 12 to confirm the information represented. Represented information may also include alarms and/or alarm and error messages. Such alarms and messages may for example be communicated to the patient by text messages, acoustic signals (buzzer), vibrations or other suitable ways. The user interface therefore also comprises instruments which generate acoustic signals and vibrations.

The patient device 2 and the operating device 4 are in communication via a transmission link 10. Depending on the configuration of the devices the patient system 1, the transmission link 10 may be configured for wireless data transmission. The user interface of the patient device 2 can therefore be represented on the operating device 4, so that a patient can operate the patient device 4 discreetly from a distance. In the exemplary embodiment shown in FIG. 1, the transmission link 10 is configured for wireless and bidirectional data transmission.

In one exemplary embodiment, data can be interchanged via the transmission link 10 according to the Bluetooth® standard (serial port profile (SSP)) with an application layer protocol placed above. The Bluetooth standard has been developed for the wireless communication of voice and data in close range, and operates with a transmission rate of up to 1 Mbit per second in the 2.45 GHz range. In another exemplary embodiment, the transmission may take place according to the IrDA, WLAN (802.11x), Zigbee, WiMax or Mics protocol.

In the exemplary embodiment shown, as mentioned, the patient device 2 is an insulin pump. The display 6 indicates the adjusted basal rate (1.0) in FIG. 1.

In other exemplary embodiments, the display 6 in normal operation may additionally show information such as the unit of the basal rate (U/h) and the time. The patient can operate the patient device 2 via menu control with the buttons 12, for example adjusting the basal rate or releasing a bolus. During operation of the patient device 2, the display 6 shows a user menu.

The operating device 4 in FIG. 1 is configured in the form of a schematically shown mobile telephone. The display 8 likewise shows the basal rate (1.0) adjusted on the patient device 2. As will be explained in more detail below, the display 8 represents an image of the readout on the display 6. The patient can operate the patient device 2 from a distance via the keypad 14 and the menu represented on the display 6. Depending on the configuration of the operating device 4 (e.g., a special device, combined device, etc.) the keypad 14 may comprise selection buttons (for example MENU, SELECT, OK, UP and DOWN, etc.) and a kind of joystick or other suitable input or controller. The operating device 4 may furthermore or alternatively support various input and output methods, for example function buttons, touchscreen, voice, acoustic and visual signals, etc.

Figure 2:
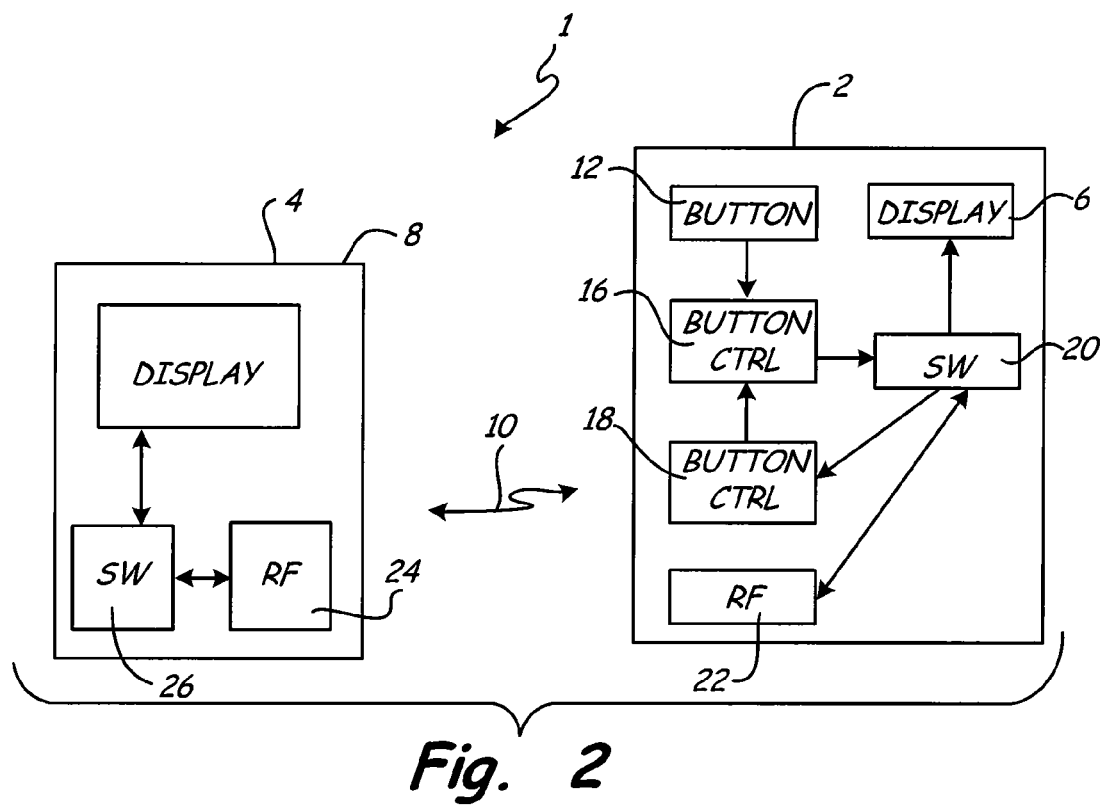
FIG. 2 shows the patient system of FIG. 1 with details of the patient device and the operating device.

FIG. 2 shows the patient system 1 of FIG. 1, additional details of the patient device 2 and the operating device 4 being shown schematically and by way of example. The patient device 2 has various modules besides the already mentioned display 6 and the buttons 12. A data-processing module 20 is used for communication with the operating interface and contains the main program or software, which controls the pump and the display 6 as a function of the button entries and sets up a display readout. The data-processing module 20 generates data for driving the pixels of a display to represent information on it. To this end, the data-communication module 20 is in direct or indirect communication with a plurality of modules 16, 18, 22. The module 16 processes the button entries which are made on the patient device 2 with the aid of the buttons 12 or on the operating device 4. The module 16 receives the button entries made on the operating device 4 preprocessed from the module 18. The module 18 receives the button entries made on the operating device 4 as data signals corresponding to this input from the data-processing module 20 which is in connection with the module 22, or communication module 22.

In one exemplary embodiment, the communication module 22 transmits and receives data according to the Bluetooth® standard. For example, the communication module 22 transmits the current display readout pixel-by-pixel to the operating device 4. The communication module 22 furthermore receives data from the operating device 4, which correspond, for example, to a function selected by pressing a button. These data are subsequently processed by the module 18.

Besides the display, the operating device 4 also has a program module 26 and a communication module 24, which operates according to the same or complementary standard/protocol as the communication module 22 and is used for communication with the communication module 22 of the patient device 2. The program module 26 generally controls the operating device 4 and therefore also the display 8.

The patient system 1 may be regarded as a client-server system, the patient device 2 being the server and the operating device 4 being the client. The patient system 1 can be operated in a "push" mode or a "request" mode. In push mode, the patient device 2 behaves as a "push" server. The information on the patient device 2 may change during use, for example because of an error message or an alarm (for example a blockage alarm). When the information on the patient device 2 changes (for example, to a display readout, alarm (buzzer, vibration)), the corresponding data are transmitted automatically from the patient device 2 to the operating device 4 and implemented there; for example, information is represented or an alarm is activated, i.e. for example the operating device 4 begins to buzz or vibrate. In some embodiments, the operating device 4 is therefore passive and waits until the most up-to-date information is transmitted to it.

In some embodiments, the patient device 2 is passive in "request" mode, i.e. the patient device 2 does not transmit data by itself to the operating device 4. In this mode, the operating device 4 may independently request information from the patient device 2, for example periodically.

In some embodiments, the application layer protocol implemented in the patient system 1 is command-oriented. In one exemplary embodiment, for example, the following commands may be transmitted from the operating device 4 to the patient device 2: start/end remote control mode, request display data, request info text, request buzzer data and request vibration data, transmit keystrokes and set mode (push or request) etc. In a similar way, for example, the following commands may be transmitted from the patient device 2 to the operating device 4: display data, info text, buzzer data and vibration data, etc.

Figure 3:
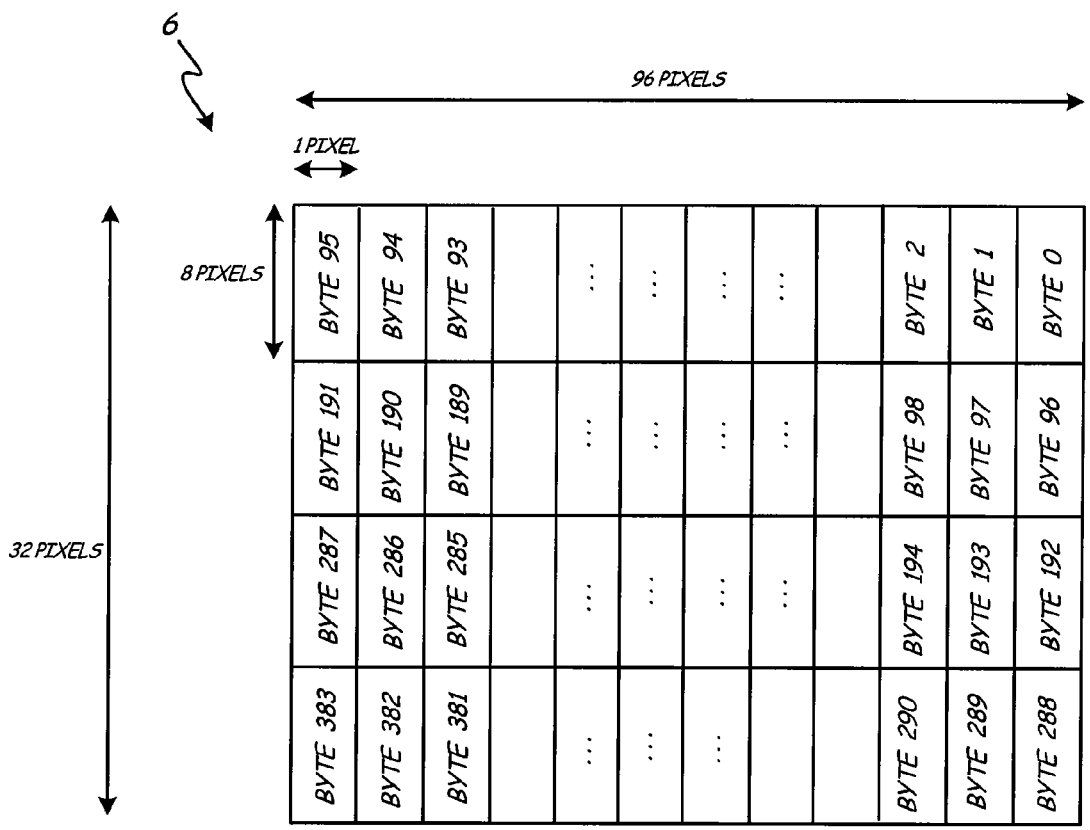
FIG. 3 is a schematic representation of a display unit.

When the patient device 2 receives the "request display data" command from the operating device 4, or when the display content has changed in "push" mode, the patient device 2 transmits the current content of the display 6 to the operating device 4 with the "display data" command. In this context FIG. 3 shows a schematic representation of the display 6, which is constructed from individual pixels. The display has 32×96 pixels in the exemplary embodiment shown, eight pixels respectively being encodable in one byte. For a monochrome display, each pixel is either black or white. This gives 384 bytes ((32×96)/8) per display content. As shown in the exemplary embodiment of FIG. 3, the display 6 consists of four rows, each row covering an area of 96×8 pixels.

In some embodiments, the patient device 2 transmits the display content row-by-row to the operating device 4. In one exemplary embodiment, after receiving a first "show display data" command (RequestDisplayData (0)), the patient device 2 transmits the first row (bytes 0-95) and then the next respective row after each further command. Once all four rows have been transmitted, the patient device 2 responds to the next command (RequestDisplayData (4)) by transmitting all of the display data (384 bytes).

The operating device 4 therefore receives an image of the current display readout from the patient device 2, and represents this image pixel-by-pixel on its display 8. In the embodiment shown in FIG. 1, this display is restricted to displaying the value 1.0. In some exemplary embodiments, the image on the display 8 could be supplemented with additional information, for example by displaying the unit of the basal rate in U/h and the current time. The display on the operating device 4 is therefore more comprehensive than that on the patient device 2. In a "minimal embodiment" of the patient device 2, the display 6 may therefore be relatively small or omitted entirely.

In a further exemplary embodiment of a patient system in accordance with the present invention, the operating device 4 may be combined with a glucose meter as the patient device. Similarly as in the patient device 2 described above, the user interface of the glucose meter may be represented on the operating device 4. If the operating device 4 is combined with a mobile telephone, for example, the glucose meter may be coupled to it wirelessly or via an interface device. The glucose meter can therefore make do without its own display. A measured glucose value can then be shown on the display 8. If in an exemplary embodiment the patient device 2 described above (insulin pump) is part of this patient system, the patient can read this value conveniently and discreetly modify the pump adjustment on the operating device 4, if necessary.

If the operating device 4 is integrated in a mobile telephone, in one exemplary embodiment, the mobile telephone may, for example, evaluate the insulin pump parameters and the measured glucose value. If the evaluation reveals that a medically alarming status exists, the mobile telephone may transmit an alarm to an emergency centre or a doctor via the mobile network. Appropriate measures to treat the patient medically may then be implemented.

The exemplary embodiments of a patient system having at least one patient device and an operating device, as described above, allow the user interface of the patient device to be relocated fully or only partially into the operating device. The patient can therefore adjust and operate the patient device conveniently and discreetly from a distance. The freedom to operate the patient device 4 directly is nevertheless preserved.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A patient system comprising a first patient device having a unitary first housing which is portable on the body of a patient and a second patient device having a second housing device arranged remotely from the first patient device, each patient device having a communication device for data transmission via a transmission link, the first patient device having a first user interface for the first patient device and a data-processor for communication with the first user interface for the first patient device, and the second patient device being configured such that a second user interface for the second patient device represents the first user interface, wherein the data-processor generates pixel address data that represents information on a display unit of the first user interface, and wherein the communication device of the first patient device transmits these data to the communication device of the second patient device to represent the information on a display unit of the second user interface;

wherein the first patient device is a medicinal substance pump with the first user interface disposed in the unitary first housing and the data-processor disposed fully into the unitary first housing; and the second user interface is disposed in the second housing;

wherein the patient system can be operated in a push mode, a request mode, and by the patient via operating buttons of the first patient device, wherein the push mode comprises correspondence of the data from the first patient device to the second patient device automatically, the request mode comprises periodic requests from the second device to the first device, and wherein the operating buttons are configured so the patient can confirm information by pressing the operating buttons.

2. The patient system according to claim 1, wherein the second patient device represents further information, including at least one of alarms or alarm and error messages.

3. The patient system according to claim 1, wherein the data-processor generates data to cause a device in the second patient device to generate at least one of an acoustic alarm or a vibration alarm.

4. The patient system according to claim 1, wherein the second user interface comprises at least one input apparatus, and wherein the communication device of the second patient device transmits data corresponding to an input to the first patient device.

5. The patient system according to claim 1, wherein the communication devices are configured such that they can transmit and receive radio signals.

6. The patient system according to claim 1, wherein the second patient device comprises a mobile telephone or a computer.

7. A method for operating a patient system comprising:
providing a first patient device having a unitary first housing portable on the body of a patient, wherein the first patient device is a medicinal substance pump;
providing a second patient device having a second housing arranged remotely from the first patient device, wherein the first patient device and second patient device are configured to communicate with one another via a transmission link;
operating a data-processor in the first patient device for communication with a first user interface for the first patient device; and
communicating pixel address data relating to the first user interface between the first and second patient devices;
wherein the pixel address data is transmitted byte-wise by the first patient device;
wherein each byte corresponds to an area on a display unit of the first user interface so as to provide a display representation of the first patient device on a display unit of the second user interface;
wherein the first user interface is disposed in the unitary first housing and the data-processor is disposed fully into the unitary first housing; and
wherein the second user interface is disposed in the second housing; and
wherein the patient system can be operated in a push mode, a request mode, and by the patient via operating buttons of the first patient device, wherein the push mode comprises correspondence of the data from the first patient device to the second patient device automatically, the request mode comprises periodic requests from the second device to the first device, and wherein the operating buttons are configured so the patient can confirm information by pressing the operating buttons.

8. The method according to claim 7, wherein the pixel address data is generated by the data-processor to represent information on a display unit of the first user interface, and wherein the pixel address data is transmitted to the second patient device to represent the information on the display unit of the second user interface.

9. The method according to claim 8, wherein the second user interface comprises at least one input, and wherein data corresponding to this input is transmitted to the first patient device.

10. The method according to claim 7, wherein data is generated in the first patient device to cause an instrument in the second patient device to generate at least one of an acoustic alarm or a vibration alarm.

11. The method according to claims 7, wherein the pixel address data is transmitted from the first patient device to the second patient device upon a change of information relating to the first patient device.

12. The method according to claim 7, wherein at least one command is transmitted from the second patient device to request data relating to the first user interface.

13. A patient system comprising:
a first patient device having a unitary first housing which is portable on the body of a patient, the first patient device comprising a first processor, a first user interface, and a first communication device for data transmission via a transmission link, wherein the first processor is operatively coupled to the first user interface and the first communication device, wherein the first user interface is disposed in the unitary first housing and the first processor is fully disposed into the unitary first housing; and
a second patient device having a second housing arranged remotely from the first patient device, the second patient device comprising a second processor, a second user interface, and a second communication device for data transmission via the transmission link, wherein the second processor is operatively coupled to the second user interface and the second communication device, wherein the second user interface is disposed in the second housing;
wherein the first processor is adapted to execute computer implemented instructions to:
generate pixel address data that represents an image on a display unit of the first user interface, and
transmit the pixel address data pixel-by-pixel, via the first communication device, to the second communication device,
wherein the second processor is adapted to execute computer implemented instructions to:
receive the pixel address data, and
display the image on the second user interface, and
wherein the first patient device is a medicinal substance pump; and
wherein the patient system can be operated in a push mode, a request mode, and by the patient via operating buttons of the first patient device, wherein the push mode comprises correspondence of the data from the first patient device to the second patient device automatically, the request mode comprises periodic requests from the second device to the first device, and wherein the operating buttons are configured so the patient can confirm information by pressing the operating buttons.

14. The patient system of claim 13, wherein the image comprises a current display readout of the first patient device.

15. The patient system of claim 1 wherein the second user interface comprises at least one input apparatus which represents at least one input apparatus of the first user interface.

16. The method of claim 7 wherein the second patient device further comprises a second user interface comprising at least one input apparatus which represents at least one input apparatus of the first user interface.

17. The patient system of claim 13 wherein the second user interface comprises at least one input apparatus which represents at least one input apparatus of the first user interface.

18. The patient system of claim 1 wherein the first patient device is a server and the second patient device is a client.

19. The method of claim 7 wherein the first patient device is a server and the second patient device is a client.

20. The patient system of claim 13 wherein the first patient device is a server and the second patient device is a client.

21. The patient system according to claim 1 wherein the second patient device is configured to send a command to the first patient device to set the mode to the push mode or the request mode, and configured to start and end a remote control mode.

* * * * *

UNITED STATES PATENT AND TRADEMARK OFFICE
CERTIFICATE OF CORRECTION

PATENT NO.      : 8,758,240 B2                                  Page 1 of 1
APPLICATION NO. : 11/608936
DATED           : June 24, 2014
INVENTOR(S)     : Marcel Frikart et al.

It is certified that error appears in the above-identified patent and that said Letters Patent is hereby corrected as shown below:

In the Claims

Col. 8, Line 5, Claim 11,
    "11. The method according to claims 7, wherein the pixel" should read
    --11. The method according to claim 7, wherein the pixel--.

Signed and Sealed this
Seventh Day of April, 2015

Michelle K. Lee
*Director of the United States Patent and Trademark Office*